United States Patent
Bennett et al.

(10) Patent No.: US 9,101,580 B2
(45) Date of Patent: Aug. 11, 2015

(54) COMPOSITIONS AND METHODS FOR TREATING TRAUMATIC BRAIN INJURY

(71) Applicants: Matthew Bennett, Toronto (CA); Gus Peller, Toronto (CA)

(72) Inventors: Matthew Bennett, Toronto (CA); Gus Peller, Toronto (CA)

(73) Assignees: Matthew Bennett, Vancouver (CA); Gus Peller, Toronto (CA)

( * ) Notice: Subject to any disclaimer, the term of this patent is extended or adjusted under 35 U.S.C. 154(b) by 0 days.

(21) Appl. No.: 13/718,065

(22) Filed: Dec. 18, 2012

(65) Prior Publication Data
US 2014/0170211 A1   Jun. 19, 2014

(51) Int. Cl.

| | | |
|---|---|---|
| *A61K 9/48* | (2006.01) | |
| *A61K 36/16* | (2006.01) | |
| *A61K 31/12* | (2006.01) | |
| *A61K 31/122* | (2006.01) | |
| *A61K 31/185* | (2006.01) | |
| *A61K 31/197* | (2006.01) | |
| *A61K 31/198* | (2006.01) | |
| *A61K 31/202* | (2006.01) | |
| *A61K 31/205* | (2006.01) | |
| *A61K 31/352* | (2006.01) | |
| *A61K 31/353* | (2006.01) | |
| *A61K 31/385* | (2006.01) | |
| *A61K 31/4045* | (2006.01) | |
| *A61K 31/685* | (2006.01) | |
| *A61K 31/7004* | (2006.01) | |

(52) U.S. Cl.
CPC .............. *A61K 36/16* (2013.01); *A61K 31/12* (2013.01); *A61K 31/122* (2013.01); *A61K 31/185* (2013.01); *A61K 31/197* (2013.01); *A61K 31/198* (2013.01); *A61K 31/202* (2013.01); *A61K 31/205* (2013.01); *A61K 31/352* (2013.01); *A61K 31/353* (2013.01); *A61K 31/385* (2013.01); *A61K 31/4045* (2013.01); *A61K 31/685* (2013.01); *A61K 31/7004* (2013.01)

(58) Field of Classification Search
None
See application file for complete search history.

(56) References Cited

U.S. PATENT DOCUMENTS

| | | | | |
|---|---|---|---|---|
| 6,197,340 | B1 * | 3/2001 | Byrd et al. | 424/468 |
| 7,635,469 | B2 * | 12/2009 | Prasad et al. | 424/94.1 |
| 7,745,486 | B2 * | 6/2010 | Lines | 514/457 |
| 7,972,633 | B2 * | 7/2011 | Smith | 424/725 |
| 2005/0042311 | A1 * | 2/2005 | Lee et al. | 424/767 |
| 2005/0059610 | A1 * | 3/2005 | Wischmeyer et al. | 514/19 |
| 2005/0222093 | A1 * | 10/2005 | Pearlman et al. | 514/114 |
| 2007/0015686 | A1 * | 1/2007 | Heuer et al. | 514/2 |
| 2007/0160659 | A1 * | 7/2007 | Platt et al. | 424/451 |
| 2008/0020995 | A1 * | 1/2008 | Purpura et al. | 514/58 |
| 2008/0213401 | A1 * | 9/2008 | Smith | 424/657 |
| 2008/0305096 | A1 * | 12/2008 | Verdegem et al. | 424/94.4 |
| 2009/0175936 | A1 * | 7/2009 | Rohr | 424/464 |
| 2010/0310538 | A1 * | 12/2010 | Wessel | 424/94.1 |

FOREIGN PATENT DOCUMENTS

| | | | |
|---|---|---|---|
| CA | 2396533 | A1 | 7/2001 |
| CA | 2550130 | A1 | 6/2005 |
| CA | 2714422 | A1 | 8/2009 |
| CA | 2480987 | C | 6/2011 |
| JP | 2008214338 | A * | 9/2008 |

OTHER PUBLICATIONS

Petraglia et al., "Stuck at the bench: Potential natural neuroprotective compounds for concussion", Surgical Neurology International, Oct. 12, 2011, <http://www.ncbi.nlm.nih.gov/pmc/articles/PMC3205506/>.

Richards, "How to Recover from a Concussion—Athletes Take Note", Byron J. Richards Wellness resources, Jul. 29, 2011, <http://www.wellnessresources.com/health/articles/how_to_recover_from_a_concussion_athletes_take_note/>.

Thorne, "Vitamin K & Headaches", LiveStrong.com, Jul. 26, 2011, <www.livestrong.com/article/501911-vitamin-k-headaches/>.

* cited by examiner

*Primary Examiner* — Robert A Wax
*Assistant Examiner* — Olga V Tcherkasskaya
(74) *Attorney, Agent, or Firm* — Philip C. Mendes da Costa; Bereskin & Parr LLP/S.E.N.C.R.L., s.r.l.

(57) ABSTRACT

The disclosure provides compositions treating traumatic brain injuries such as concussions. In one embodiment, the composition comprises phosphatidylserine, phosphatidylcholine, quercetin, astaxanthin, R-alpha lipoic acid, N-acetyl cysteine, taurine, L-glutamine, carnitine, D-ribose, creatine, epigallocatechin gallate, melatonin, ginkgo leaf extract, curcumin and L-glycine. The disclosure also provides methods for treating traumatic brain injuries such as concussions by administering an effective amount of the compositions described within.

9 Claims, 6 Drawing Sheets

Figure 7
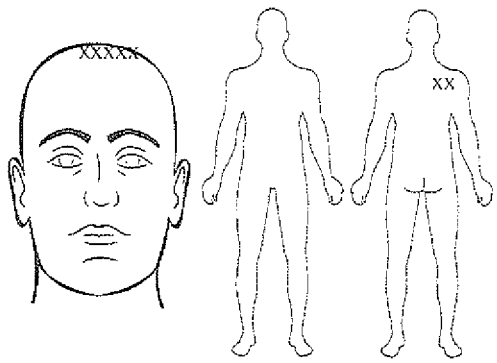
Figure 7
Figure 8
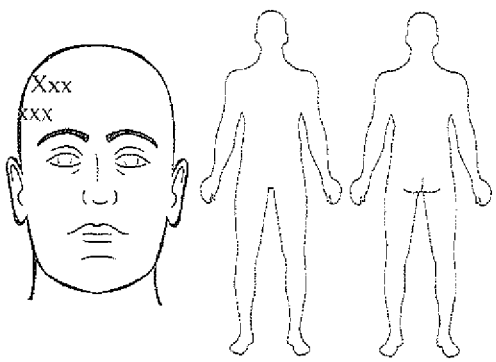
Figure 9
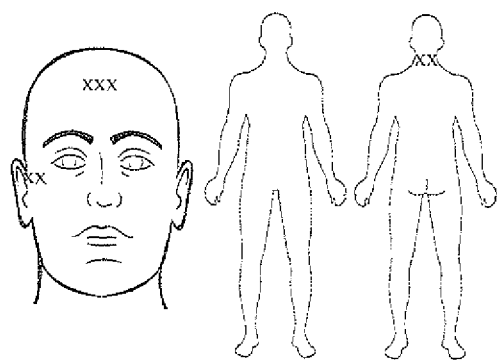

COMPOSITIONS AND METHODS FOR TREATING TRAUMATIC BRAIN INJURY

FIELD

The disclosure relates to compositions and methods for treating traumatic brain injuries such as concussions.

INTRODUCTION

A traumatic brain injury (TBI) occurs when an external mechanical force causes damage to the brain. Traumatic brain injuries are classified based on severity, the anatomical features of the injury, and the mechanism of the injury.

Concussions are one of the most common forms of traumatic brain injury. It has been estimated that as many as 3.8 million sports and recreation-related concussions occur in the United States each year. A concussion can be defined as a complex pathophysiological process affecting the brain, induced by traumatic biomechanical forces.

Several common features that incorporate clinical, pathological and biomechanical injury constructs that may be utilized in defining the nature of a concussive head injury include: (1) Concussion may be caused either by a direct blow to the head, face or neck or a blow elsewhere on the body with an "impulsive" force transmitted to the head. (2) Concussion typically results in the rapid onset of short-lived impairment of neurologic function that resolves spontaneously. (3) Concussion may result in neuropathological changes but the acute clinical symptoms largely reflect a functional disturbance rather than a structural injury. (4) Concussion results in a graded set of clinical symptoms that may or may not involve loss of consciousness. Resolution of the clinical and cognitive symptoms typically follows a sequential course. In a small percentage of cases, however, post-concussive symptoms may be prolonged. (5) No abnormality on standard structural neuroimaging studies is seen in concussion.

Concussions may result in a variety of symptoms including headache, physical impairment (for example, unsteadiness), cognitive impairment (for example, confusion or memory loss) and abnormal behavior. Traditionally, concussions have been treated through physical and cognitive rest.

Traumatic brain injuries such as concussions are complex and involve a constellation of signs and symptoms that vary from patient to patient. While the identification of concussions has improved in recent years, there remains a need for improved treatment.

SUMMARY

The present inventors have discovered that a specific combination of natural products improves symptoms of a traumatic brain injury and accelerates healing.

Accordingly, in one broad aspect of the disclosure, a composition is provided comprising at least 8 components selected from the group consisting of: phosphatidylserine, phosphatidylcholine, quercetin, astaxanthin, R-alpha lipoic acid, N-acetyl cysteine, taurine, L-glutamine, carnitine, D-ribose, creatine, epigallocatechin gallate, melatonin, ginkgo leaf extract, curcumin, and L-glycine.

An advantage of this composition is that it serves several functions, namely it limits inflammation, improves energy production (supports mitochondrial function by increasing ATP production and enhancing energy cellular processes such as the Electron Transport Chain), augments circulation, restores capillary integrity, acts as a neuro-protective and cytoprotective agent by limiting oxidative stress, and promotes repair of damaged cervical musculature and connective tissue. Accordingly, the composition is useful for reducing the duration and/or severity of concussive symptoms.

In one embodiment, the composition comprises 50-4500 mg phosphatidylserine, 100-4500 mg phosphatidylcholine, 100-2000 mg quercetin, 0.5-12 mg astaxanthin, 100-4000 mg R-alpha lipoic acid, 100-5000 mg N-acetyl cysteine, 500-8000 mg taurine, 500-50000 mg L-glutamine, 500-30000 mg carnitine, 500-30000 mg D-ribose, 500-30000 mg creatine, 50-5000 mg epigallocatechin gallate, 0.1-15 mg melatonin, 50-1000 mg ginkgo leaf extract, 100-3000 mg curcumin, and/or 500-6000 mg L-glycine. In one embodiment, the composition comprises phosphatidylserine, phosphatidylcholine, quercetin, R-alpha lipoic acid, L-glutamine, taurine, carnitine and D-ribose. In another embodiment, the composition comprises astaxanthin, N-acetyl cysteine, creatine, epigallocatechin gallate, melatonin, ginkgo leaf extract, curcumin and L-glycine.

In a further embodiment, the composition comprises phosphatidylserine, phosphatidylcholine, quercetin, astaxanthin, R-alpha lipoic acid, N-acetyl cysteine, taurine, L-glutamine, carnitine, D-ribose, creatine, epigallocatechin gallate, melatonin, ginkgo leaf extract, curcumin, and L-glycine.

In another embodiment, the composition is an oral composition. Optionally, the oral composition is in a solid, semi-solid, gel, paste, liquid, crystalline or encapsulated form. In a further embodiment, the oral form is a capsule or a tablet.

In yet another embodiment, the composition further comprises at least one component selected from the group consisting of omega 3 fatty acids, co enzyme Q10, vitamin K1, vitamin K2, magnesium, potassium, zinc, L-theanine, vitamin B1, vitamin B2, vitamin B3, vitamin B5, vitamin B6, vitamin B9, vitamin B12, vitamin C, vitamin E, valine, leucine, isoleucine and resveratrol.

In another broad aspect of the disclosure, a method of treating traumatic brain injury, for example a concussion, in a subject is provided, wherein the method comprises administering an effective amount of a composition comprising at least 8 components selected from the group consisting of: phosphatidylserine, phosphatidylcholine, quercetin, astaxanthin, R-alpha lipoic acid, N-acetyl cysteine, taurine, L-glutamine, carnitine, D-ribose, creatine, epigallocatechin gallate, melatonin, ginkgo leaf extract, curcumin, and L-glycine to the subject.

In one embodiment, 50-4500 mg phosphatidylserine, 100-4500 mg phosphatidylcholine, 100-2000 mg quercetin, 0.5-12 mg astaxanthin, 100-4000 mg R-alpha lipoic acid, 100-5000 mg N-acetyl cysteine, 500-8000 mg taurine, 500-50000 mg L-glutamine, 500-30000 mg carnitine, 500-30000 mg D-ribose, 500-30000 mg creatine, 50-5000 mg epigallocatechin gallate, 0.1-15 mg melatonin, 50-1000 mg ginkgo leaf extract, 100-3000 mg curcumin, and/or 500-6000 mg L-glycine is administered to the subject.

In one embodiment, a composition comprising phosphatidylserine, phosphatidylcholine, quercetin, R-alpha lipoic acid, L-glutamine, taurine, carnitine and D-ribose is administered to the subject. In another embodiment, a composition comprising astaxanthin, N-acetyl cysteine, creatine, epigallocatechin gallate, melatonin, ginkgo leaf extract, curcumin and L-glycine is administered to the subject.

In a further embodiment, a composition comprising phosphatidylserine, phosphatidylcholine, quercetin, astaxanthin, R-alpha lipoic acid, N-acetyl cysteine, taurine, L-glutamine, carnitine, D-ribose, creatine, epigallocatechin gallate, melatonin, ginkgo leaf extract, curcumin, and L-glycine is administered to the subject.

In a further embodiment, the composition is administered once a day to the subject. Optionally, the composition is administered once a day for at least one, two, three, four, five or six, twelve or twenty-four months.

In another embodiment, the composition is administered orally to the subject.

In another broad aspect of the disclosure, a use of a composition comprising at least 8 components selected from the group consisting of: phosphatidylserine, phosphatidylcholine, quercetin, astaxanthin, R-alpha lipoic acid, N-acetyl cysteine, taurine, L-glutamine, carnitine, D-ribose, creatine, epigallocatechin gallate, melatonin, ginkgo leaf extract, curcumin, and L-glycine for treating traumatic brain injury is provided. Optionally, the traumatic brain injury is a concussion.

In one embodiment, a composition comprising phosphatidylserine, phosphatidylcholine, quercetin, R-alpha lipoic acid, L-glutamine, taurine, carnitine and D-ribose is for use for treating traumatic brain injury. In another embodiment, a composition comprising astaxanthin, N-acetyl cysteine, creatine, epigallocatechin gallate, melatonin, ginkgo leaf extract, curcumin and L-glycine is for use for treating traumatic brain injury.

In a further embodiment, a composition comprising phosphatidylserine, phosphatidylcholine, quercetin, astaxanthin, R-alpha lipoic acid, N-acetyl cysteine, taurine, L-glutamine, carnitine, D-ribose, creatine, epigallocatechin gallate, melatonin, ginkgo leaf extract, curcumin, and L-glycine is for use for treating traumatic brain injury.

In another aspect of the disclosure, a method is provided for preparing a composition for treating traumatic brain injury comprising combining at least 8 components selected from the group consisting of: phosphatidylserine, phosphatidylcholine, quercetin, astaxanthin, R-alpha lipoic acid, N-acetyl cysteine, taurine, L-glutamine, carnitine, D-ribose, creatine, epigallocatechin gallate, melatonin, ginkgo leaf extract, curcumin, and L-glycine to obtain the composition.

In one embodiment, the method comprises combining phosphatidylserine, phosphatidylcholine, quercetin, R-alpha lipoic acid, L-glutamine, taurine, carnitine and D-ribose to obtain the composition. In another embodiment, the method comprises combining astaxanthin, N-acetyl cysteine, creatine, epigallocatechin gallate, melatonin, ginkgo leaf extract, curcumin and L-glycine to obtain the composition.

In a further embodiment, phosphatidylserine, phosphatidylcholine, quercetin, astaxanthin, R-alpha lipoic acid, N-acetyl cysteine, taurine, L-glutamine, carnitine, D-ribose, creatine, epigallocatechin gallate, melatonin, ginkgo leaf extract, curcumin, and L-glycine are combined to obtain the composition.

DESCRIPTION OF DRAWINGS

FIGS. 1-18 are drawings depicting the location of a subject's pain.

DETAILED DESCRIPTION

I. Definitions

Figure 1:
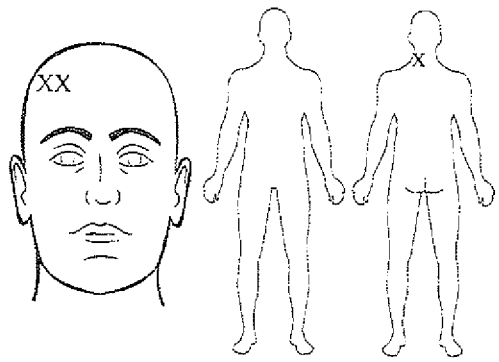

The terms "composition" and "pharmaceutical composition" as used herein are equivalent terms referring to a composition of matter for pharmaceutical use.

The term "component" as used herein refers an ingredient that is combined with additional components/ingredients to obtain a composition. In some embodiments, the component or ingredient is a nutraceutical. In other embodiments, the component or ingredient is a natural product, namely a chemical compound or substance that is produced by a living organism. In further embodiments, the component or ingredient is a plant or animal extract. The components described herein may be obtained from natural sources or may be chemically synthesized.

The term "traumatic brain injury" as used herein refers to an injury that occurs when an external mechanical force causes damage to the brain. The force may be internal or external. For example, a traumatic brain injury can result when the head suddenly and violently hits an object, or when an object pierces the skull and enters brain tissue. Symptoms of a traumatic brain injury can be mild, moderate, or severe, depending on the extent of the damage to the brain.

The term "concussion" as used herein refers to a type of traumatic brain injury that is caused by a direct or indirect mechanism, for example a direct blow to the head, face or neck or a blow elsewhere on the body with an "impulsive" force transmitted to the head. A concussion is characterized by an immediate and transient alteration in brain function, including alteration of mental status and level of consciousness. Diagnosis of concussion includes one or more of the following clinical domains. Symptoms include (a) somatic (e.g. Headache), cognitive (e.g. Feeling like in a fog, dullness) and/or emotional symptoms (e.g. lability, depression) (b) physical signs (e.g. loss of consciousness, amnesia, convulsions), (c) behavioural changes (e.g. irritability), (d) cognitive impairment (e.g. slowed reaction times), (e) sleep disturbance (e.g. drowsiness). Sequelae of concussion include recurrent concussion, migraine headaches, depression, Parkinson's disease, Alzheimer's disease, attention deficit hyperactivity disorder, learning disability, sleep disorders, neurotransmitter production disturbance (e.g. dopamine, serotonin, acetylcholine, GABA).

The term "effective amount" as used herein means an amount sufficient to achieve the desired result and accordingly will depend on the ingredient and its desired result. Nonetheless, once the desired effect is known, determining the effective amount is within the skill of a person skilled in the art. For example, as used herein an "effective amount of the composition" is optionally the amount of composition that is sufficient to treat a subject who has suffered a traumatic brain injury.

The term "pharmaceutically acceptable" means compatible with the treatment of animals, in particular, humans.

The terms "treating" or "treatment" as used herein, and as are well understood in the art, mean an approach for obtaining beneficial or desired results, including clinical results. Beneficial or desired clinical results can include, but are not limited to, alleviation or amelioration of one or more symptoms or conditions, diminishment of extent of injury or disease, stabilizing (i.e. not worsening) the state of injury or disease, delaying or slowing of injury or disease progression, amelioration or palliation of the injury or disease state, diminishment of the reoccurrence of injury or disease, and remission (whether partial or total), whether detectable or undetectable. Treatment methods optionally comprise administering to a subject a therapeutically effective amount of a composition and optionally consists of a single administration, or alternatively comprise a series of applications. The length of the treatment period depends on a variety of factors, such as the severity of the condition, the age of the patient, the concentration of the composition and components of the composition, the activity of the compositions and components of the composition, and/or a combination thereof. It will also be appreciated that the effective dosage of the composition and components of the composition used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions may be administered to the subject in an amount and for a duration sufficient to treat the patient.

The term "subject" as used herein includes all members of the animal kingdom, including mammals, and suitably refers to humans.

II. Compositions

The present disclosure includes a composition comprising a number of individual components. In one embodiment, the components are natural products or nutraceuticals. The composition is particularly useful for treating traumatic brain injuries such as concussions. Without being bound by theory, it is believed that the compounds described below act synergistically to reduce inflammation, improve cellular energy production, promote circulation and capillary integrity, limit oxidative stress and augment healing of damaged cervical musculature and connective tissue.

In one embodiment, the composition comprises at least 3, 4, 5, 6, 7, 8, 9, 10, 11, 12, 13, 14 or 15 components selected from the group consisting of phosphatidylserine, phosphatidylcholine, quercetin, astaxantin, R-Alpha Lipoic Acid, N-Acetyl cysteine, taurine, L-glutamine, carnitine, D-Ribose, creatine, epigallocatechin gallate, melatonin, ginkgo leaf extract, curcumin and L-glycine. In yet another embodiment, the composition consists of, or consists essentially of, at least 3, 4, 5, 6, 7, 8, 9, 10, 11, 12, 13, 14 or 15 components selected from the group consisting of phosphatidylserine, phosphatidylcholine, quercetin, astaxantin, R-Alpha Lipoic Acid, N-Acetyl cysteine, taurine, L-glutamine, carnitine, D-Ribose, creatine, epigallocatechin gallate, melatonin, ginkgo leaf extract, curcumin and L-glycine.

In one embodiment, the composition comprises phosphatidylserine, phosphatidylcholine, quercetin, astaxantin, R-Alpha Lipoic Acid, N-Acetyl cysteine, taurine, L-glutamine, carnitine, D-Ribose, creatine, epigallocatechin gallate, melatonin, ginkgo leaf extract, curcumin and L-glycine. In another embodiment, the composition consists of, or consists essentially of, phosphatidylserine, phosphatidylcholine, quercetin, astaxantin, R-Alpha Lipoic Acid, N-Acetyl cysteine, taurine, L-glutamine, carnitine, D-Ribose, creatine, epigallocatechin gallate, melatonin, ginkgo leaf extract, curcumin and L-glycine.

In another embodiment, the composition comprises or consists essentially of phosphatidylserine, phosphatidylcholine, quercetin, R-alpha lipoic acid, L-glutamine, taurine, carnitine and D-ribose and suitable carriers, diluents, flavoring additives and other standard additives.

In a further embodiment, the composition comprises or consists essentially of astaxanthin, N-acetyl cysteine, creatine, epigallocatechin gallate, melatonin, ginkgo leaf extract, curcumin and L-glycine and suitable carriers, diluents, flavoring additives and other standard additives.

Phosphatidylserine is a component of biological membranes. Phosphatidylserine (PS) may be derived from a natural source, such as bovine cortex or soy, or chemically synthesized. Without being bound by theory, phosphatidylserine may promote nerve cell integrity. Optionally, phosphatidylserine is present in the composition in the amount of 50-4500 mg, 100-2000 mg, 200-1000 mg or approximately 300 or 400 mg.

Phosphatidylcholine is a major component of biological membranes. Phosphatidylcholine (PC) may be derived from a natural source, such as egg yolk or soy, or chemically synthesized. Without being bound by theory, phosphatidylcholine may promote nerve cell integrity. Optionally, phosphatidylcholine is present in the composition in the amount of 100-4500 mg, 500-3000 mg, 1000-2000 mg or approximately 1500 mg.

Quercetin (2-(3,4-dihydroxyphenyl)-3,5,7-trihydroxy-4H-chromen-4-one) is a plant-derived flavonoid found in fruits, vegetables, leaves and grain. Without being bound by theory, quercetin may act as an anti-inflammatory agent by limiting histamine and leukotienes which is complemented by limiting enzymes that promote the degradation of connective tissue protein and impair capillary fragility and permeability. Optionally, quercetin is present in the composition in the amount of 100-2000 mg, 200-1000 mg, or approximately 500 mg or 600 mg.

Astaxanthin (3,3'-dihydroxy-R-carotene-4,4'-dione) is a carotenoid found in a number of natural sources such as microalgae, yeast, salmon, trout, krill, shrimp, crayfish, crustaceans, and bird feathers. It can also be chemically synthesized. Without being bound by theory, astaxanthin may act as an anti-inflammatory. Optionally astaxanthin is present in the composition in the amount of 0.5-12 mg, 1-5 mg or about 2, 2.5 or 3 mg.

R-alpha lipoic acid ((R)-5-(1,2-dithiolan-3-yl)pentanoic acid) is the (R)-(+)-enantiomer of lipoic acid. While lipoic acid exists as two enantiomers, only the (R)-(+)-enantiomer is found in nature and is an essential cofactor of four mitochondrial enzyme complexes. R-alpha lipoic acid can be chemically synthesized. Without being bound by theory, R-alpha lipoic acid may act as a cytoprotective agent by reducing oxidative stress to lipids, proteins and DNA, as well as improving memory retention by acting on dopamine D2 receptors. Optionally, R-alpha lipoic acid is present in the composition in the amount of 100-4000 mg, 200-2000 mg, 400-1000 mg or approximately 800 mg or 1000 mg.

N-Acetyl cysteine (2-Acetamido-3-sulfanylpropanoic acid) is a nutritional supplement used primarily as a mucolytic agent. Without being bound by theory, N-Acetyl cysteine may act as an anti-oxidant as a precursor to glutathione, an inflammatory cytokine. Optionally, N-Acetyl cysteine is present in the composition in the amount of 100-5000 mg, 200-2000 mg, 400-1000 mg or approximately 400, 800, 900 or 1200 mg.

Taurine (2-aminoethanesulfonic acid) is an organic acid and a major constituent of bile. Without being bound by theory, taurine may act as a cell volume regulator and cytoprotective agent in the central nervous system as it is the most abundant amino acid in the brain, retina, muscle tissue and internal organs. Optionally, taurine is present in the composition in the amount of 500-8000 mg, 500-6000 mg, 500-4000 mg, 500-2000 mg or approximately 1000 or 2000 mg.

L-Glutamine is the most abundant naturally occurring, non-essential amino acid in nature. L-Glutamine aids in tissue repair as a precursor to neurotransmitters such as GABA and has been shown to be useful in treatment of various injuries. Optionally, L-Glutamine is present in the composition in the amount of 500-50000 mg, 1000-10000 mg, 2000-5000 mg or approximately 3000, 3500 or 5000 mg.

Carnitine is biosynthesized from the amino acids lysine and methionine. In cells, it is required for the generation of metabolic energy. Without being bound by theory, carnitine may promote oxygen uptake and tissue repair. Optionally, carnitine is present in the composition in the amount of 500-30000 mg, 1000-10000 mg, 2000-5000 mg or approximately 2000 mg or 3000 mg.

D-Ribose is an enantiomer of ribose. Only the D-enantiomer of ribose is found in nature. Ribose is a simple sugar of formula $C_5H_{10}O_5$. Without being bound by theory, D-ribose may promote oxygen uptake and tissue repair as well as supports mitochondrial energy production for synthesis of adenosine triphosphate. Optionally, D-ribose is present in the composition in the amount of 500-30000 mg, 1000-10000 mg, 2000-5000 mg or approximately 2000 mg or 3000 mg.

Creatine (2-(Methylguanidino)ethanoic acid) is a nitrogenous organic acid that occurs naturally in vertebrates. It helps to supply energy to cells. Without being bound by theory, creatine may promote oxygen uptake and tissue repair. Optionally, creatine is present in the composition in the amount of 500-30000 mg, 1000-10000 mg, 2000-5000 mg or approximately 2000 mg or 3000 mg.

Epigallocatechin gallate (also known as ECGC) is found in green tea extract. It is a potent anti-oxidant. Optionally, ECGC is present in the composition in the amount of 50-5000 mg, 100-2000 mg, 100-1000 mg, 100-500 mg or approximately 180 or 300 mg.

Melatonin (N-acetyl-5-methoxytryptamine) is a hormone secreted by the pineal gland in the brain. It is often used as a sleep aid by regulating circadian rhythm and enhancing immune function. Optionally, melatonin is present in the composition in the amount of 0.1-15 mg, 0.5-10 mg, 1-5 mg or approximately 3 mg.

Extracts of ginkgo leaves (ginkgo leaf extract) contain flavonoid glycosides and terpenoids. Ginkgo leaf extract has been used as a memory and concentration enhancer, as well as an antivertigo agent. Ginkgo enhances arterial and capillary flow, increases cerebral glucose metabolism and limits the decline of serotonin receptors. It also acts as an anti-oxidant and anti-inflammatory. Optionally, ginkgo leaf extract is present in the composition in the amount of 50-1000 mg, 100-500 mg or approximately 200 mg.

Curcumin is the principal curcuminoid of the spice turmeric. Without being bound by theory, curcumin may act as inflammatory agent, increase aerobic capacity and modulate numerous cellular signaling pathways such as inflammatory cytokine production and apoptotic proteins in the present compositions. Optionally, curcumin is present in the composition in the amount of 100-3000 mg, 200-2000 mg, 300-1000 mg or approximately 500 or 800 mg.

L-glycine is an amino acid. Without being bound by theory, L-glycine may act as an anti-oxidant and potentiates N-methyl-D-aspartate receptor-mediated neurotransmission in the present compositions. Optionally, L-glycine is present in the composition in the amount of 500-6000 mg, 1000-5000 mg or 2000-4000 mg or approximately 3000 mg.

Optionally, the composition further comprises omega 3 fatty acids, co enzyme Q10, vitamin K1, vitamin K2, magnesium, potassium, zinc, L-theanine, vitamin B1, vitamin B2, vitamin B3, vitamin B5, vitamin B6, vitamin B9, vitamin B12, vitamin C, vitamin E, valine, leucine, isoleucine and resveratrol and mixtures thereof.

In one embodiment, the composition comprises the following components: phosphatidylserine, phosphatidylcholine, omega-3, vitamin D3, quercetin, astaxantin, coenzyme Q10, L-glutamine, L-glycine, taurine, carnitine, creatine, D-ribose, vitamin K2, magnesium, potassium, zinc, L-theanine, vitamin B complex (B1, 2, 3, 5, 6, 9, 12), vitamin C and vitamin E. In another embodiment, the composition comprises 50-4500 mg phosphatidylserine, 100-4500 mg phosphatidylcholine, 500-2000 mg omega-3, 500-2000 mg vitamin D3, 100-2000 mg quercetin, 0.5-12 mg astaxantin, 50-200 mg coenzyme Q10, 500-50000 mg L-glutamine, 500-6000 mg L-glycine, 500-8000 mg taurine, 500-30000 mg carnitine, 500-30000 mg creatine, 500-30000 mg D-ribose, 20-80 mg vitamin K2, 200-1000 mg magnesium, 25-150 mg potassium, 5-50 mg zinc, 10-2000 mg L-theanine, 10-50 mg vitamin B complex (B1, 2, 5, 6, 9, 12), 500-2000 mg vitamin C and 50-500 mg vitamin E.

In one embodiment, the composition comprises astaxanthin, L-Glutamine, phosphatidylserine, Omega 3 fatty acids, N-acetyl cysteine, vitamin C and magnesium. In another embodiment, the composition comprises 0.5-12 mg astaxantin, 500-50000 mg L-Glutamine, 50-4500 mg phosphatidylserine, 500-2000 mg Omega 3 fatty acids, 100-5000 mg N-acetyl cysteine, 500-2000 mg vitamin C and 200-1000 mg magnesium.

In some embodiments, the composition is formulated for administration to a subject such as a human. In particular embodiments, the composition is formulated for oral administration.

Optionally, the composition is formulated for inhalative, rectal or parenteral administration, including dermal, intradermal, intragastral, intracutaneous, intravasal, intravenous, intramuscular, intraperitoneal, intranasal, intravaginal, intrabuccal, percutaneous, subcutaneous, sublingual, topical or transdermal administration.

The compositions for oral administration optionally include, but are not limited to, solid, semi-solid, gel, paste, liquid, crystalline or encapsulated forms. Non-limiting examples of these forms include capsules, tablets, suspensions, powders, suspended-release formulations, solutions, emulsions and syrups. In further embodiments, the composition is used as an inhalant or suppository. In one embodiment, the compositions for oral administration range from 5 to 50,000 g, optionally 10 to 1000 g or 15 to 250 g.

In some embodiments, the composition is formulated such that a single dose is contained in one capsule or tablet or gel pack. In other embodiments, the composition is formulated such that a single dose is contained in at least 2, 3, 4 or more individual capsules, tablets, packet, or packets.

In other embodiments, the composition includes a pharmaceutically acceptable carrier, excipient, buffer or stabilizer. Suitable pharmaceutically acceptable carriers include essentially chemically inert and nontoxic materials that do not interfere with the effectiveness of the biological activity of the pharmaceutical composition. Suitable vehicles are described, for example, in Remington's Pharmaceutical Sciences (Remington's Pharmaceutical Sciences, 20th ed., Mack Publishing Company, Easton, Pa., USA, 2000). Examples of suitable pharmaceutical carriers include, but are not limited to, water, saline solutions, glycerol solutions, ethanol, N-(1(2,3-dioleyloxy)propyl)N,N, N-trimethylammonium chloride (DOTMA), diolesylphosphotidyl-ethanolamine (DOPE), and liposomes. Such compositions contain a therapeutically effective amount of the components in the composition, together with a suitable amount of carrier so as to provide the form for direct administration to the patient.

The composition may also include flavour and/or colour additives. For example, beet powder may be added for flavor.

III. Methods and Uses of the Composition

The disclosure includes methods for treating a traumatic brain injury comprising administering an effective amount of the compositions described herein to a subject in need thereof. The disclosure also includes the use of the compositions described here for treating a subject who has suffered a traumatic brain injury.

In one embodiment, the traumatic brain injury is a concussion. Accordingly, the disclosure also relates to methods for treating a concussion comprising administering an effective amount of the compositions described herein to a subject in need thereof. The disclosure also relates to the use of the compositions described here for treating a subject who has suffered a concussion.

In one embodiment, the present methods are used for treating a subject who has at least 1, 2, 3, 4 or 5 concussion symptoms. Concussion symptoms include, but are not limited to, headache, pressure in head, neck pain, nausea or vomiting, dizziness, blurred vision, sensitivity to light, sensitivity to noise, feeling slowed down, feeling "in a fog", "not feeling right", difficulty concentrating, difficulty remembering, fatigue or low energy, confusion, drowsiness, trouble falling asleep, increased emotions, irritability sadness and nervousness or anxiety. Optionally, the present methods are used for treating a subject who has been diagnosed with a traumatic brain injury or a concussion.

In another embodiment, the present methods are used for treating a post-concussive syndrome. Post-concussive syndromes include, but are not limited to, post-concussion disease, prolonged post-concussion disease, mild cognitive impairment, chronic traumatic encephalopathy and dementia pugilistica. In further embodiments the present methods are used for treating long-term complications of concussion such as Alzheimers disease, Parkinsons disease, amyotrophic lateral sclerosis (ALS) or post concussive depression.

In an embodiment, the composition is administered once a day to a subject in need thereof. In another embodiment, the composition is administered every other day, every third day or once a week. In another embodiment, the composition is administered twice a day. In still another embodiment, the composition is administered three times a day or four times a day. In a further embodiment, the composition is administered at least once a day for at least 1, 2, 3, 4, 5, 6, 7, 8, 9, 10, 11 or 12 weeks. In still a further embodiment, the composition is administered at least once a day for a longer term such as at least 4, 6, 8, 10, 12 or 24 months. Administration in one embodiment includes but is not limited to a dosage of 10-50 mg of composition at a frequency of minimum 1, 2, 3 or 4 times per day. Optionally, administration continues until all symptoms are resolved and cleared by medical personnel via standardized testing such as SCAT 2.

In one embodiment, the composition is administered within 1, 2, 3, 5 or 7 days of the traumatic brain injury. In other embodiments, the composition is administered within 1, 2, 3, 5 or 7 days of the appearance of symptoms of a traumatic brain injury.

In one embodiment, the composition is administered at least once a day until the condition has ameliorated to where further treatment is not necessary. In another embodiment, the composition is administered until all symptoms of the traumatic brain injury are resolved. In another embodiment, the composition is administered until the subject is able to return to physical activity or "cleared to play" in a particular sport.

In an even further embodiment, the composition is administered for at least 1, 2, 3, 6, 8, 10 or 12 or 24 months after the subject is asymptomatic. Optionally, the composition is administered for at least 1, 2, 3, 6, 8, 10 or 12 or 24 months after the subject is able to return to physical activity or "cleared to play" in a particular sport.

The compositions of the present disclosure are useful and effective when administered to treat a traumatic brain injury such as a concussion. The amount of each component present in the composition will be the amount that is therapeutically effective, i.e., an amount that will result in the effective treatment of the condition (e.g., traumatic brain injury) when administered. The therapeutically effective amount will vary depending on the subject and the severity and nature of the injury and can be determined routinely by one of ordinary skill in the art.

In one embodiment, 50-4500 mg phosphatidylserine, 100-4500 mg phosphatidylcholine, 100-2000 mg quercetin, 0.5-12 mg astaxanthin, 100-4000 mg R-alpha lipoic acid, 100-5000 mg N-acetyl cysteine, 500-8000 mg taurine, 500-50000 mg L-glutamine, 500-30000 mg carnitine, 500-30000 mg D-ribose, 500-30000 mg creatine, 50-5000 mg epigallocatechin gallate, 0.1-15 mg melatonin, 50-1000 mg ginkgo leaf extract, 100-3000 mg curcumin, and/or 500-6000 mg L-glycine is administered to a subject to treat a traumatic brain injury such as a concussion.

It will also be appreciated that the effective dosage of the composition and the individual components of the composition for the treatment may increase or decrease over the course of a particular treatment regime. In some instances, chronic administration may be required.

Also contemplated within the present disclosure is the use of compositions described herein as a preventive or prophylactic measure against a traumatic brain injury such as concussion. In some embodiments, the compositions are administered to a subject prior to a traumatic brain injury. The disclosure also includes methods for treating subjects who are at risk of a traumatic brain injury or who have previously suffered from a traumatic brain injury comprising administering to the subjects an effective amount of the compositions described herein. In other embodiments, the compositions are used for treating a subject who is suspected of having a traumatic brain injury or a subject who may have suffered from a traumatic brain injury. The subject may or may not display symptoms of a traumatic brain injury.

EXAMPLES

Example 1

Nutraceutical Combinations to Treat Concussive Brain Trauma

A study was conducted whereby subjects with concussive brain trauma were treated with various combinations of the components described herein.

Methods

Eighteen study participants (15 males and 3 females, aged 15 through 45 and comprising 15 athletes and 3 non-athletes) diagnosed with a concussive injury were treated with different combinations of the compounds discussed herein. Adjuvant soft tissue mobilization and acupuncture were used as indicated. All concussion subjects completed the Sport Concussion Assessment Tool 2 (SCAT 2) survey at intervals during their injury to characterize and grade their symptoms. For athletes, concussion duration was calculated in days from the date of injury until the athlete was medically cleared to resume competitive play (athlete needed to be asymptomatic to resume competitive play). Of the 3 non-athletes, one subject fell resulting in an associated concussive injury and the two other subjects were injured in a motor vehicle accident. For these subjects, the duration of the concussion was calculated from the date of injury in days until the study participant was completely asymptomatic. Athletes with a previous concussion estimated the time they were withheld from sports with their previous head injury whereas, the three non-sports related concussion subjects estimated their duration of symptoms with their previous concussion if applicable.

Results

Patient Evaluation and Treatment Data (A) BC1201

Male subject BC1201 (18 years old) was injured on Aug. 16, 2012 by a soccer ball to the face.

The location of the subject's pain is depicted in FIG. 1.

The symptoms associated with the injury were: Headache, "Pressure in the head", Neck pain, Dizziness, Blurred vision, Balance issues, Sensitivity to light and noise, "Don't feel right", Difficulty concentrating, Confusion, Drowsiness and Anxiety. The injury severity was rated 6/10.

The subject had previously experienced brain trauma in May 2011 that lasted 84 days (12 weeks). The injury severity was rated 6/10. Previous treatments were rest and massage and ingestion of a multivitamin at an unknown dose. Compared to the previous injury, the recent injury had increased sensitivity to noise and light.

The subject took the following nutraceuticals daily: Quercetin—500 mg; Alpha lipoic acid—800 mg; Carnitine—3000 mg; Ribose—3000 mg.

The subject's symptoms resolved in 20 days and the subject returned to activity Sep. 11, 2012. A smooth return to play was noted. Headaches were reduced and energy was sustained throughout the rehabilitation process.

(B) AC1202

Male subject AC1202 (16 years old) was injured playing football on Jun. 10, 2012 by a knee to the left side of the head.

Figure 2:
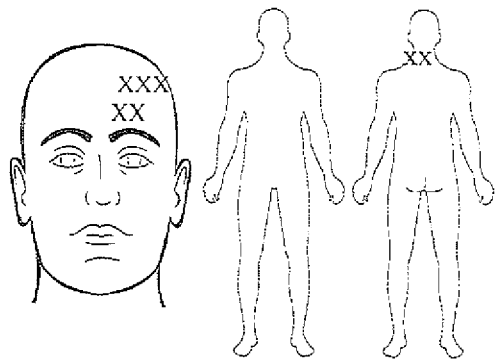

The location of the subject's pain is depicted in FIG. 2.

The symptoms associated with the injury were: Headache, "Pressure in the head", Neck pain, Nausea, Balance problems, Sensitivity to light and noise, "Don't feel right", Difficulty concentrating, Fatigue, Drowsiness (morning) and Irritability. The injury severity was rated 8110.

The subject had previously experienced brain trauma in October 2011 that lasted 56 days (8 weeks). The injury severity was rated 7/10. Previous treatments were rest and administration of Vitamin C (1000 mg) and Vitamin D3 (2000 IU). Compared to the previous injury, the recent injury had increased sensitivity to noise and light, increased fatigue and neck pain due to the mechanism of the injury.

The subject took the following nutraceuticals daily: Omega 3 fatty acids—1800 mg; Vitamin D—4000 IU; Quercetin 600 mg; Astaxanthin—2.5 mg; Curcumin—500 mg.

The subject's symptoms resolved in 8 days and the subject returned to activity Jun. 20, 2012. Bruising was resolved within 3 days.

(C) DS1203

Male subject DS1203 (15 years old) was injured playing rugby on May 8, 2012 by head to head contact.

Figure 3:
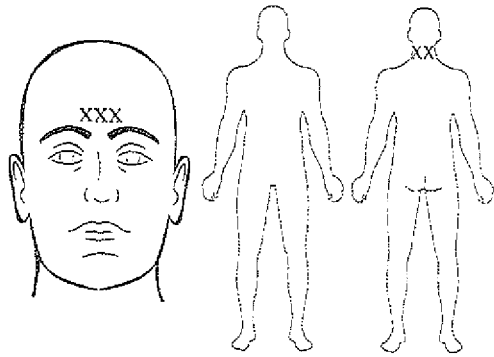

The location of the subject's pain is depicted in FIG. 3.

The symptoms associated with the injury were: Headache, "Pressure in the head", Neck pain, Balance problems, Sensitivity to light and noise, "Don't feel right", Low energy with activity. The injury severity was rated 8/10.

The subject had not experienced previous brain trauma.

The subject took the following nutraceuticals daily: Phosphatidylcholine—1500 mg; Phosphatidylserine—400 mg; Quercetin—500 mg; Taurine—1000 mg; ECGC—180 mg.

The subject's symptoms resolved in 10 days and the subject returned to activity May 21, 2012. The subject reported sustained energy and no residual cognitive impairment was documented via standard testing.

(D) RS1204

Female subject RS1204 (32 years old) was injured on Jun. 26, 2012 in an automobile accident (driver).

Figure 4:
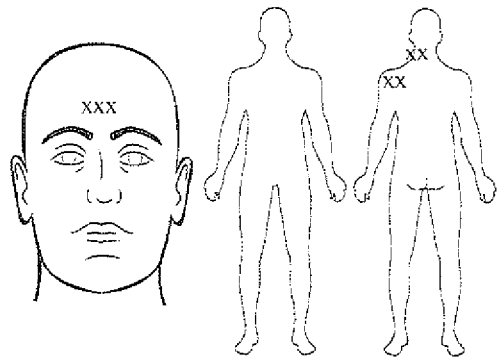

The location of pain from the injury is depicted in FIG. 4.

The symptoms associated with the injury were: Headache, Neck pain, Dizziness, Sensitivity to light and noise, feels slowed down, "in a fog", fatigue following activity, confusion with direction, drowsiness with reading, irritability. The injury severity was rated 6/10.

The subject had previously experienced brain trauma in Feb. 10, 2011 that lasted 77 days (11 weeks). The injury severity was rated 8/10. Previous treatments included chiropractic adjustment and continued ingestion of whey protein and multivitamins. Compared to the previous injury, the recent injury had less headache but increased fatigue and concentration difficulty.

The subject took the following nutraceuticals daily: Glycine—3000 mg; Ribose—2000 mg; Glutamine—3000 mg; N-acetyl cysteine—800 mg; Carnitine—3000 mg; Quercetin—500 mg.

The subject's symptoms resolved in 7 days and the subject returned to activity Jul. 8, 2012. Residual neck tension was the longest symptom.

(E) MR1205

Male subject MR1205 (16 years old) was injured playing hockey on Apr. 6, 2012 by helmet-to-helmet contact.

Figure 5:
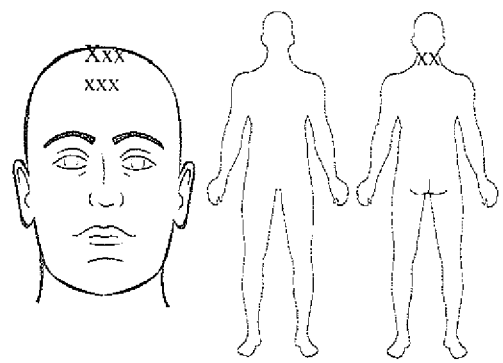

The location of the subject's pain is depicted in FIG. 5.

The symptoms associated with the injury were: Headache, "Pressure in the head", Neck pain, Nausea, Dizziness with movement, Balance problems, Sensitivity to light and noise, feels slowed down, "Don't feel right", Fatigue, Drowsiness. The injury severity was rated 7/10.

The subject had previously experienced brain trauma in Aug. 15, 2010 that lasted 70 days (10 weeks). The injury severity was 5/10. Previous treatments were rest, acupuncture, massage and maintained ingestion of Omega 3 fatty acids and whey protein (unknown dose). Compared to the previous injury, the recent injury included increased headaches.

The subject took the following nutraceuticals daily: Creatine—2000 mg; Melatonin—3 mg (before bed); Alpha Lipoic Acid—800 mg; Phosphatidylserine—300 mg; Phosphatidylcholine—1500 mg; Astaxanthin—2 mg.

The subject's symptoms resolved in 12 days and the subject returned to activity Apr. 20, 2012. Melatonin was recommended for sleep disturbance. Phospholipids were recommended for benefit in proprioceptive disturbance.

(F) BL1206

Male subject BL1206 (17 years old) was injured playing soccer on Jul. 8, 2012 by an elbow to the head.

Figure 6:
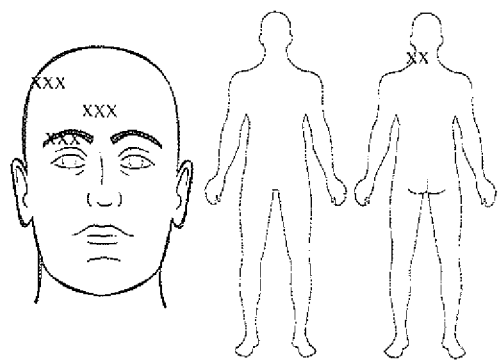

The location of the subject's pain is depicted in FIG. 6.

The symptoms associated with the injury were: Headache, "Pressure in head", Neck pain, Nausea, Dizziness, Blurred Vision, Balance Problems, "In a fog", "Don't feel right", Difficulty concentrating, Fatigue with activity, Irritability. The injury severity was rated 9/10.

The subject had previously experienced brain trauma in April 2010 that lasted 42 days (6 weeks). The injury severity was rated 7/10. The previous treatment was rest. Blurred vision and fatigue appeared to be increased in the recent injury The subject took the following nutraceuticals daily: Quercetin—500 mg; Astaxanthin—3 mg; Alpha Lipoic Acid—1000 mg; Phosphatidylserine—300 mg; Phosphatidylcholine—1500 mg; Ribose—2000 mg.

The subject's symptoms resolved in 12 days and the subject returned to activity Jul. 26, 2012. Quercetin was used in this application because of its anti-inflammatory properties.

(G) BS1207

Male subject BS1207 (44 years old) was injured by a fall from height, direct to head/neck on Aug. 12, 2012.

The location of the subject's pain is depicted in FIG. 7.

The symptoms associated with the current injury were: Headache, Neck pain, Nausea, Dizziness, Blurred Vision, Sensitivity to light and noise, Feels slowed down, "in a fog", "Don't feel right", Difficulty concentrating and remembering, low energy throughout the day, drowsiness, Irritability, increased anxiety. The injury severity was rated 8/10.

The subject had previously experienced brain trauma in September 2008 that lasted 70 days (10 weeks). The injury severity was rated 8/10. The previous treatment was rest. The constellation of symptoms and symptom severity was very similar between the recent and the previous injury.

The subject took the following nutraceuticals daily: N-acetyl cysteine—900 mg; Glutamine—3500 mg; Glycine—3000 mg; Quercetin—500 mg; Curcumin—800 mg.

The subject's symptoms resolved in 10 days and the subject returned to activity Aug. 30, 2012.

(H) DM1208

Female subject DM1208 (48 years old) was injured playing indoor soccer on Mar. 16, 2012 by a ricochet of a ball to the side of the head.

The location of the subject's pain is depicted in FIG. 8.

The symptoms associated with the injury were: Headache, "Pressure in head", Dizziness with movement, Balance Problems, Sensitivity to light and noise, Feels slowed down, Difficulty concentrating, Fatigue, Drowsiness, increased emotional response, Irritability, Sadness, increased anxiety. The injury severity was rated 8/10.

The subject had previously experienced brain trauma on Nov. 10, 2011 that lasted 84 days (12 weeks). The injury severity was 7/10. Previous treatments were rest, chiropractic adjustment and anti-depressant medication. The recent injury had increased vertigo and co-ordination issues particularly in vehicles.

The subject took the following nutraceuticals daily: Omega 3 fatty acids—1800 mg, Phosphatidylcholine—1500 mg; Phosphatidylserine—400 mg; Astaxanthin—3 mg.

The subject's symptoms resolved in 15 days and the subject returned to activity Apr. 4, 2012. Problematic headaches and poor concentration addressed with blend of omega fatty acids, phospholipids and anti-oxidants.

(I) JH1209

Male subject JH1209 (31 years old) was injured playing hockey on Mar. 26, 2012 by an elbow to chin.

The location of the subject's pain is depicted in FIG. 9.

The symptoms associated with the current injury were: Headache, "Pressure in the head", Neck pain, Dizziness, Balance problems, Sensitivity to noise, "In a fog", "Don't feel right", Difficulty concentrating, Fatigue, Drowsiness, Increased emotional response, Increased irritability, Increased anxiety. The injury severity was rated 6/10.

The subject had previously experienced brain trauma in February 2009 that lasted 68 days (24 weeks). The injury severity was rated 6/10. The previous treatment was rest. The recent injury was of approximately the same intensity as the previous injury, the only difference is the presence of "in a fog" with the recent injury.

The subject took the following nutraceuticals daily: Carnitine—2000 mg; Glycine—3000 mg; Melatonin—3 mg; Ginkgo leaf extract—200 mg; N-Acetyl Cysteine—400 mg.

The subjects symptoms resolved in 12 days and the subject returned to activity Apr. 11, 2012. Melatonin was recommended to address sleep disturbance.

(J) KP1210

Male subject KP1210 (19 years old) was injured playing soccer on Aug. 16, 2012 by a knee to the chin.

Figure 10:
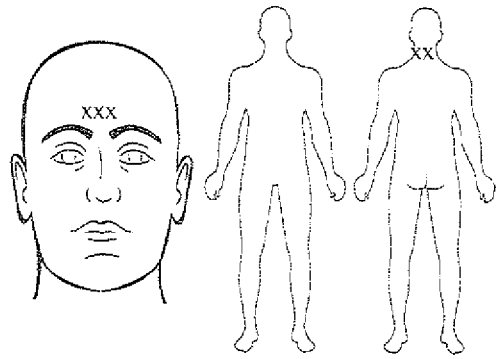

The location of the subject's pain is depicted in FIG. 10.

The symptoms associated with the injury were: Headache, "Pressure in the head", Neck pain, Nausea, Dizziness, Fatigue with mental activity. The injury severity was rated 9/10.

The subject had previously experienced brain trauma on Jan. 15, 2012 that lasted 35 days (5 weeks). The injury severity was rated 7110. Previous treatments were rest and massage and ingestion of the following nutraceuticals: Amino acids, omega 3 fatty acids, combo vitamin C/E (unknown dose). Increased headache was seen with the recent injury.

The subject took the following nutraceuticals daily: Phosphatidylserine—400 mg; Phosphatidylcholine—1500 mg; Quercetin—500 mg; Astaxanthin—2.5 mg; Ribose—2000 mg.

The subject's symptoms resolved in 9 days and the subject returned to activity Aug. 3, 2012. Anti-oxidants were recommended for benefit of reducing fatigue and improving concentration.

(K) FG1211

Male subject FG1211 (17 years old) was injured playing soccer on Aug. 3, 2012 by a foot to the forehead.

Figure 11:
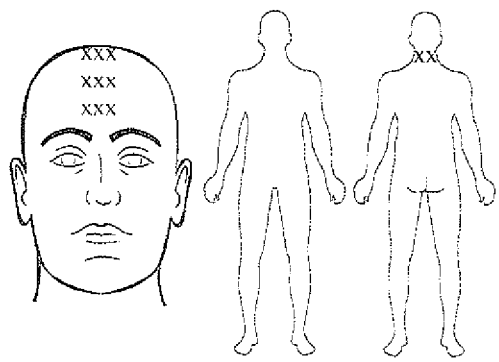

The location of the subject's pain is depicted in FIG. 11.

The symptoms associated with the injury were: Headache, "Don't feel right", Difficulty concentrating, low energy with motivation, Confusion with daily tasks, Drowsiness, Irritability, Increased anxiety. The injury severity was rated 8/10.

The subject had not experienced previous brain trauma.

The subject took the following nutraceuticals daily: Glutamine—3500 mg; Taurine—2000 mg; Carnitine—2000 mg.

The subject's symptoms resolved in 11 days and the subject returned to activity Aug. 17, 2012. Residual confusion may have resolved more promptly with the addition of omega-3 fatty acids.

(L) MK1212

Male subject MK1212 (20 years old) was injured playing football on Jul. 6, 2012 by helmet to helmet contact.

Figure 12:
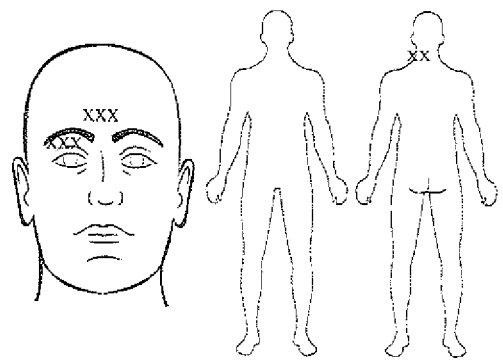

The location of the subject's pain is depicted in FIG. 12.

The symptoms associated with the injury were: Headache, "Pressure in the head", Neck pain, Sensitivity to light and noise, "In a fog", Fatigue with mental exertion, increased irritability, Increased sadness. The injury severity was rated 8/10.

The subject had previously experienced brain trauma in March 2010 that lasted 98 days (14 weeks). The injury severity was rated 4/10. The previous treatment was rest. Depression, neck pain and headache were increased in the recent injury.

The subject took the following nutraceuticals daily: Curcumin 500 mg; Quercetin—500 mg; Astaxanthin—2.5 mg; Omega 3 fatty acids—1800 mg.

The subject's symptoms resolved in 20 days and the subject returned to activity Jul. 28, 2012.

(M) JJ1213

Male subject JJ1213 (22 years old) was injured playing soccer on Jun. 18, 2012 by head to head contact.

Figure 13:
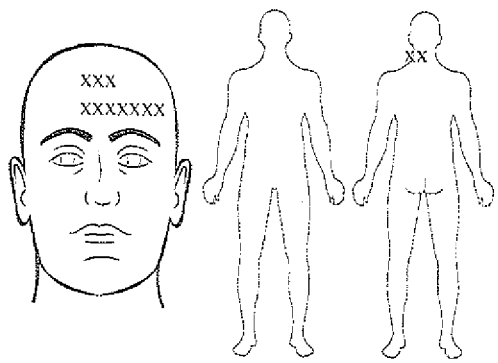

The location of the subject's pain is depicted in FIG. 13.

The symptoms associated with the injury were: Headache, "Pressure in the head", Neck pain, Dizziness, Blurred vision, Balance problems, Sensitivity to light and noise, Feels slowed down, "In a fog", "Don't feel right", Fatigue, Confusion, Drowsiness, Increased emotion, Increased irritability and anxiety. The injury severity was rated 6/10.

The subject had previously experienced brain trauma in April 2007 that lasted 42 days (6 weeks). The injury severity was rated 5/10. The previous treatment was rest and ingestion of a Multivitamin (active formula), Vitamin C (2000 mg) and Whey protein. The recent injury resulted in increased emotional disturbance and sensitivity to noise.

The subject took the following nutraceuticals daily: Glutamine—5000 mg, Phosphatidylcholine—1500 mg, Phosphatidylserine—400 mg; Ribose—2000 mg.

The subject's symptoms resolved in 6 days and the subject returned to activity Jun. 28, 2012. A quick recovery and full return to play was noted.

(N) JL1214

Male subject JL1214 (18 years old) was injured playing football on Jul. 12, 2012 by helmet-to-helmet contact.

Figure 14:
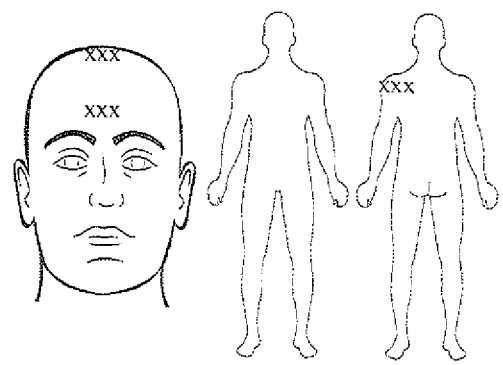

The location of the subject's pain is depicted in FIG. 14.

The symptoms associated with the injury were; Headache, Neck pain, Blurred vision, Balance problems, Feels slowed down, "In a fog", "Don't feel right", increased irritability and nervousness. The injury severity was rated 5/10.

The subject had previously experienced brain trauma in September 2011 that lasted 21 days (3 weeks). The injury severity was rated 8/10. The previous treatment was rest. The previous injury had increased fatigue and nausea.

The subject took the following nutraceuticals daily: Glutamine—5000 mg; Quercetin—500 mg; Astaxanthin—2.5 mg; Alpha lipoic acid—1000 mg; Carnitine—3000 mg, ECGC—300 mg.

The subject's symptoms resolved in 5 days and the subject returned to activity Jul. 21, 2012. A full return to play with quick resolution of symptoms was noted. Glutamine and quercetin were used to treat the predominant symptom of headache.

(O) MR1215

Male subject MR1215 (26 years old) was injured on Aug. 4, 2012 by swimming/diving.

Figure 15:
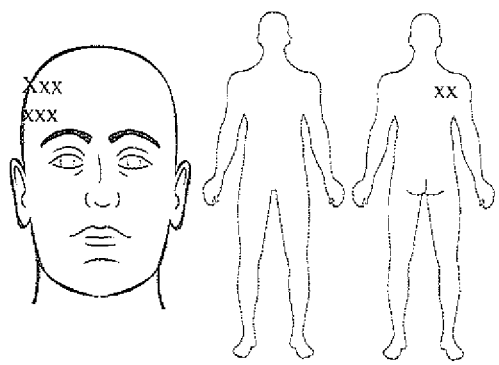

The location of the subject's pain is depicted in FIG. 15.

The symptoms associated with the injury were: Headache, Neck pain, Dizziness, Balance problems, Sensitivity to noise, "Don't feel right". The injury severity was rated 7/10.

The subject had not previously experienced brain trauma.

The subject took the following nutraceuticals daily: Glutamine—5000 mg; Taurine—2000 mg; Carnitine—3000 mg, Creatine—2000 mg; Phosphatidylcholine—1500 mg; Phosphatidylserine—400 mg.

The subject's symptoms resolved in 16 days and the subject returned to activity Aug. 22, 2012.

(P) MV1216

Female subject MV1216 (34 years old) was injured on May 11, 2012 in an automobile accident (passenger).

Figure 16:
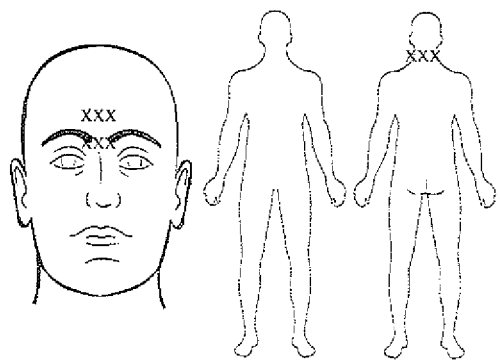

The location of the subject's pain is depicted in FIG. 16.

The symptoms associated with the injury were: Headache, "Pressure in the head", Neck pain, Dizziness, Blurred vision, Balance problems, Sensitivity to light and noise, "In a fog", "Don't feel right", Difficulty concentrating and remembering, Fatigue with exertion, Increased irritability. The injury severity was rated 6/10.

The subject had previously experienced brain trauma in May 2010 that lasted 21 days (3 weeks). The injury severity was rated 6/10. The previous treatment was rest and ingestion of Omega 3 fatty acids (1000 mg), Vitamin D (400 IU), Vitamin C (1000 mg) and a Multivitamin.

The subject took the following nutraceuticals daily: Omega 3 fatty acids—1800 mg; Phosphatidylcholine 1500 mg; Phosphatidylserine—400 mg; Astaxanthin—2.5 mg; Quercetin—500 mg; Ribose—2000 mg.

The subject's symptoms resolved in 13 days and the subject returned to activity May 30, 2012. Neck pain resided with additional manual massage. Quercetin and phospholipids were used because of their anti-inflammatory properties.

(Q) JM1217

Male subject JM1217 (17 years old) was injured playing soccer on Jun. 29, 2012 by a ball to the back of the head.

Figure 17:
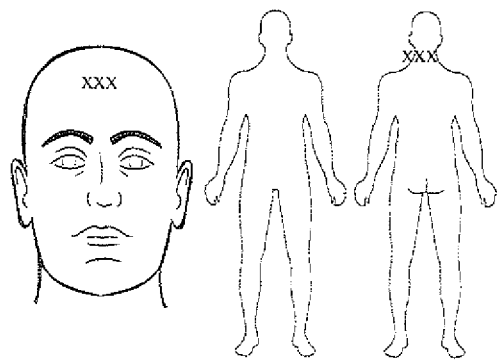

The location of the subject's pain is depicted in FIG. 17.

The symptoms associated with the injury were: Headache, "Pressure in the head", Neck pain, Sensitivity to noise, "Don't feel right", Difficulty concentrating and remembering, fatigue with exertion, increased irritability. The injury severity was rated 9/10.

The subject had previously experienced brain trauma in June 2008 that lasted 28 days (4 weeks). The injury severity was rated 7/10. The previous treatment was rest. Increased headache causing disability was noted in the recent injury.

The subject took the following nutraceuticals daily: Glutamine—5000 mg; Carnitine—3000 mg; Taurine—2000 mg; Curcumin—500 mg; Quercetin—500 mg; N-acetyl cysteine—1200 mg.

The subject's symptoms resolved in 17 days and the subject returned to activity Jul. 18, 2012.

(R) JB1218

Male subject JB1218 (20 years old) was injured playing soccer on May 24, 2012 by head to head contact.

Figure 18:
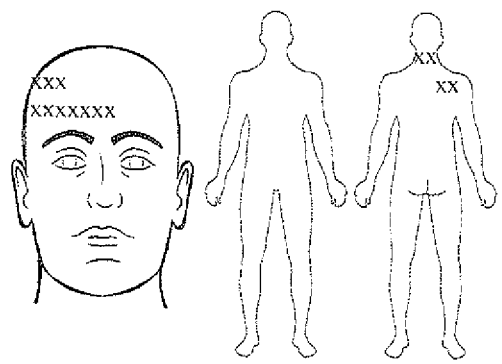

The location of the subject's pain is depicted in FIG. 18.

The symptoms associated with the injury were: Headache, "Pressure in the head", Neck pain, Sensitivity to noise, Feels slowed down, "In a fog", "Don't feel right", Fatigue with physical and mental exertion, Increased irritability, Increased sadness. The injury severity was rated 7/10.

The subject had previously experienced brain trauma in October 2009 that lasted 35 days (5 weeks). The injury severity was rated 7/10. The previous treatment was rest and a multivitamin. Increased emotional disturbance, fatigue and neck pain were noted in the recent injury.

The subject took the following nutraceuticals daily: Phosphatidylserine—400 mg; Phosphatidylcholine—1500 mg; Quercetin 500 mg; Astaxanthin—2.5 mg; Glycine—3000 mg; Carnitine—3000 mg; Taurine—2000 mg; Alpha lipoic acid—1000 mg; N-acetyl cysteine—1000 mg; Ribose—5000 mg.

The subject's symptoms resolved in 10 days and the subject returned to activity Jun. 10, 2012. A quick resolution of symptoms with no gastrointestinal side effects from the ingested formulation was noted.

Summary of Results

This was the first concussion for 3 subjects and the second concussion for 15 of the 18 subjects. For those subjects with a previous concussion, eight of the subjects graded their most recent concussion as more severe than their first concussion at the onset of symptoms; five subjects graded their second concussion as the same in severity as their previous concussion; and two subjects graded their second concussion as less severe than their previous concussion. Duration of concussion symptoms were reduced in all 15 subjects who ingested the nutraceutical formulations with their second concussion. The average duration of the initial concussion in the 15 subjects was 62.1 days. The average duration of the second concussion in the same subjects treated with nutraceuticals was 11.7 days. There was a statistically significant difference between the duration of the concussion symptoms for subjects ingesting the nutraceutical formulations and the same subjects not ingesting the nutraceutical formulations (P<0.001).

Tables 1 and 2 summarize the results of the pilot study. Table 1 compares the duration of symptoms in the study participants in their first concussion and second concussion. Table 2 provides an overview of the nutraceuticals taken by each study participant and the duration of their concussion symptoms. Amounts are in milligrams (mg) unless otherwise noted.

TABLE 1

Concussion pilot study participants

| Study Participants | Initial concussion untreated | | Second concussion treated with nutraceuticals | |
|---|---|---|---|---|
| | Symptom duration in days | Severity of concussion graded (1-10) | Symptom duration in days | Severity of concussion graded (1-10) |
| BC 1201 | 90 | 6 | 20 | 6 |
| AC 1202 | 56 | 7 | 8 | 8 |
| DS 1203 | N/A | N/A | 10 | 8 |
| RS 1204 | 77 | 8 | 7 | 6 |
| MR 1205 | 70 | 5 | 12 | 7 |
| BL 1206 | 42 | 5 | 12 | 9 |
| BS 1207 | 70 | 8 | 10 | 8 |
| DM 1208 | 84 | 7 | 15 | 8 |
| JH 1209 | 168 | 6 | 12 | 6 |
| KP 1210 | 35 | 7 | 9 | 9 |
| FG 1211 | N/A | N/A | 11 | 8 |
| MK 1212 | 98 | 4 | 20 | 8 |
| JJ 1213 | 42 | 5 | 6 | 6 |
| JL 1214 | 21 | 8 | 5 | 5 |
| MR 1215 | N/A | N/A | 16 | 7 |
| MV 1216 | 21 | 6 | 3 | 6 |
| JM 1217 | 28 | 7 | 17 | 9 |
| JB 1218 | 35 | 7 | 10 | 7 |

TABLE 2

Nutraceuticals taken by study participants

| Compound | BC 1201 | AC 1202 | DS 1203 | RS 1204 | MR 1205 | BL 1206 | BS 1207 | DM 1208 | JH 1209 |
|---|---|---|---|---|---|---|---|---|---|
| Phosphatidyl-serine | | | 400 | | 300 | 300 | | 400 | |
| Phosphatidyl-choline | | | 1500 | | 1500 | 1500 | | 1500 | |
| Quercetin | 500 | 600 | 500 | 500 | | 500 | 500 | | |
| Astaxanthin | | 2.5 | | | 2 | 3 | | 3 | |
| R-Alpha Lipoic Acid | 800 | | | | 800 | 1000 | | | |
| N-Acetyl Cysteine | | | | 800 | | | 900 | | 400 |
| Taurine | | | 1000 | | | | | | |
| L-glutamine | | | | | 3000 | | | 3500 | |
| Carnitine | 3000 | | | | 3000 | | | | 2000 |
| D-Ribose | 3000 | | | | 2000 | | 2000 | | |
| Creatine | | | | | | 2000 | | | |
| EGCG | | | 180 | | | | | | |
| Melatonin | | | | | | 3 | | | |
| Ginko Leaf Extract | | | | | | | | | 200 |
| Curcumin | | 500 | | | | | | 800 | |
| L-glycine | | | | | 3000 | | | 3000 | 3000 |
| Omega-3 fatty acids | | 1800 | | | | | | 1800 | |
| Vitamin D (IU) | | 4000 | | | | | | | |
| Length of symptoms (days) | 20 | 8 | 10 | 7 | 12 | 12 | 10 | 15 | 12 |

| Compound | KP 1210 | FG 1211 | MK 1212 | JJ 1213 | JL 1214 | MR 1215 | MV 1216 | JM 1217 | JB 1218 |
|---|---|---|---|---|---|---|---|---|---|
| Phosphatidyl-serine | 400 | | | 400 | | 400 | 400 | | 400 |
| Phosphatidyl-choline | 1500 | | | 1500 | | 1500 | 1500 | | 1500 |
| Quercetin | 500 | | 500 | | 500 | | 500 | 500 | 500 |
| Astaxanthin | 2.5 | | 2.5 | | 2.5 | | 2.5 | | 2.5 |
| R-Alpha Lipoic Acid | | | | | 1000 | | | | 1000 |
| N-Acetyl Cysteine | | | | | | | | 1200 | 1000 |
| Taurine | | 2000 | | | | 2000 | | 2000 | 2000 |
| L-glutamine | | 3500 | | 5000 | 5000 | 5000 | | 5000 | |
| Carnitine | | 3000 | | | 3000 | 3000 | | 3000 | 3000 |
| D-Ribose | 2000 | | | 2000 | | | 2000 | | 5000 |
| Creatine | | | | | | 2000 | | | |
| EGCG | | | | | | 300 | | | |
| Melatonin | | | | | | | | | |
| Ginko Leaf Extract | | | | | | | | | |
| Curcumin | | | 500 | | | | | 500 | |
| L-glycine | | | | | | | | | 3000 |

TABLE 2-continued

| Nutraceuticals taken by study participants | | | | | | | | | |
|---|---|---|---|---|---|---|---|---|---|
| Omega-3 fatty acids | | | 1800 | | | | 1800 | | |
| Vitamin D (IU) | | | | | | | | | |
| Length of symptoms (days) | 9 | 11 | 20 | 6 | 5 | 16 | 13 | 17 | 10 |

Here, the efficacy of a number of compounds in treating concussive injury was demonstrated. The compounds worked synergistically and a reduction in time away from sports activity following concussion due to a decrease in symptom duration was observed.

In particular, the efficacy of these components was remarkably illustrated with individuals with a previous history of concussion. Current medical research has established that a second concussion increases symptom duration by approximately two and a half times. In contrast, all subjects with a previous concussion treated with the components described herein experienced symptom resolution much more quickly than expected. On average, symptom duration was reduced by a multiple of 5 when a subject with a second concussion was treated with components described herein.

Accordingly, the present study provides convincing scientific evidence that the following components are efficacious for concussion treatment in a clinical setting: phosphatidylserine, phosphatidylcholine, quercetin, astaxanthin, R-alpha lipoic acid, N-acetyl cysteine, taurine, L-glutamine, carnitine, D-ribose, creatine, epigallocatechin gallate, melatonin, ginkgo leaf extract, curcumin and L-glycine.

The present study establishes the effectiveness of each of the following components for treating concussion symptoms and expediting recovery from injury: phosphatidylserine, phosphatidylcholine, quercetin, astaxanthin, R-alpha lipoic acid, N-acetyl cysteine, taurine, L-glutamine, carnitine, D-ribose, creatine, epigallocatechin gallate, melatonin, ginkgo leaf extract, curcumin and L-glycine. This study also provides evidence that a composition comprising subset of components from the group consisting of phosphatidylserine, phosphatidylcholine, quercetin, astaxanthin, R-alpha lipoic acid, N-acetyl cysteine, taurine, L-glutamine, carnitine, D-ribose, creatine, epigallocatechin gallate, melatonin, ginkgo leaf extract, curcumin and L-glycine, is useful for treating subjects with a traumatic brain injury. A composition comprising each of phosphatidylserine, phosphatidylcholine, quercetin, astaxanthin, R-alpha lipoic acid, N-acetyl cysteine, taurine, L-glutamine, carnitine, D-ribose, creatine, epigallocatechin gallate, melatonin, ginkgo leaf extract, curcumin and L-glycine is also useful for treating subjects with a traumatic brain injury.

Example 2

Formulation

Based on the surprising results of Example 1, the following compositions (designated Formulations I-III in Tables 3-5, respectively), were used to treat subjects who have suffered a traumatic brain injury.

Formulation I includes all of the components determined in Example 1 to be efficacious in treating traumatic brain injury.

Formulation II includes a subset of the components determined in Example 1 to be efficacious in treating traumatic brain injury. The subset of components were selected based on their ability to limit inflammation, improve cellular energy production, augment circulation, restore capillary integrity, act as a neuroprotective and cytoprotective agent by limiting oxidative stress and promoting repair of damaged musculature and connective tissue. Collectively, these components reduce the duration and severity of symptoms in subjects with traumatic brain injury.

Formulation III includes a second subset of the components determined in Example 1 to be efficacious in treating traumatic brain injury. The subset of components were selected based on their ability to limit inflammation, improve cellular energy production, augment circulation, restore capillary integrity, act as a neuroprotective and cytoprotective agent by limiting oxidative stress and promoting repair of damaged musculature and connective tissue. Collectively, these components reduce the duration and severity of symptoms in subjects with traumatic brain injury.

TABLE 3

Formulation I

| Component | Dosage Range (qd) |
|---|---|
| Phosphatidylserine | 50-4500 mg |
| Phosphatidylcholine | 100-4500 mg |
| Quercetin | 100-2000 mg |
| Astaxanthin | 0.5-12 mg |
| R-alpha lipoic acid | 100-4000 mg |
| N-Acetyl cysteine | 100-5000 mg |
| Taurine | 500-8000 mg |
| Glutamine | 500-50000 mg |
| Carnitine | 500-30000 mg |
| D-Ribose | 500-30000 mg |
| Creatine | 500-30000 mg |
| Epigallocatechin gallate | 50-5000 mg |
| Melatonin | 0.1-15 mg |
| Ginkgo leaf extract | 50-1000 mg |
| Curcumin | 100-3000 mg |
| L-glycine | 500-6000 mg |

TABLE 4

Formulation II

| Component | Dosage Range (qd) |
|---|---|
| Phosphatidylserine | 50-4500 mg |
| Phosphatidylcholine | 100-4500 mg |
| Quercetin | 100-2000 mg |
| R-alpha lipoic acid | 100-4000 mg |
| Taurine | 500-8000 mg |
| Glutamine | 500-50000 mg |
| Carnitine | 500-30000 mg |
| D-Ribose | 500-30000 mg |

TABLE 5

Formulation III

| Component | Dosage Range (qd) |
|---|---|
| Astaxanthin | 0.5-12 mg |
| N-Acetyl cysteine | 100-5000 mg |

TABLE 5-continued

Formulation III

| Component | Dosage Range (qd) |
|---|---|
| Creatine | 500-30000 mg |
| Epigallocatechin gallate | 50-5000 mg |
| Melatonin | 0.1-15 mg |
| Ginkgo leaf extract | 50-1000 mg |
| Curcumin | 100-3000 mg |
| L-glycine | 500-6000 mg |

What has been described above has been intended illustrative and non-limiting and it will be understood by persons skilled in the art that other variances and modifications may be made without departing from the scope of the disclosure as defined in the claims appended hereto.

The invention claimed is:

1. A method of treating a traumatic brain injury in a subject, comprising administering an effective amount of a composition comprising at least 8 components selected from the group consisting of: phosphatidylserine, phosphatidylcholine, quercetin, astaxanthin, R-alpha lipoic acid, N-acetyl cysteine, taurine, L-glutamine, carnitine, D-ribose, creatine, epigallocatechin gallate, melatonin, ginkgo leaf extract, curcumin, and L-glycine to the subject.

2. The method of claim 1, wherein 50-4500 mg phosphatidylserine, 100-4500 mg phosphatidylcholine, 100-2000 mg quercetin, 0.5-12 mg astaxanthin, 100-4000 mg R-alpha lipoic acid, 100-5000 mg N-acetyl cysteine, 500-8000 mg taurine, 500-50000 mg L-glutamine, 500-30000 mg carnitine, 500-30000 mg D-ribose, 500-30000 mg creatine, 50-5000 mg epigallocatechin gallate, 0.1-15 mg melatonin, 50-1000 mg ginkgo leaf extract, 100-3000 mg curcumin, and/or 500-6000 mg L-glycine is administered to the subject.

3. The method of claim 1, wherein phosphatidylserine, phosphatidylcholine, quercetin, R-alpha lipoic acid, L-glutamine, taurine, carnitine and D-ribose are administered to the subject.

4. The method of claim 1, wherein astaxanthin, N-acetyl cysteine, creatine, epigallocatechin gallate, melatonin, ginkgo leaf extract, curcumin and L-glycine are administered to the subject.

5. The method of claim 1, wherein phosphatidylserine, phosphatidylcholine, quercetin, astaxanthin, R-alpha lipoic acid, N-acetyl cysteine, taurine, L-glutamine, carnitine, D-ribose, creatine, epigallocatechin gallate, melatonin, ginkgo leaf extract, curcumin and L-glycine are administered to the subject.

6. The method of claim 1, wherein the traumatic brain injury is a concussion.

7. The method of claim 1, wherein the composition is administered one to three times a day to the subject.

8. The method of claim 1, wherein the composition is administered one to three times a day for at least one, two, six, twelve or twenty-four months.

9. The method of claim 1, wherein the composition is administered orally to the subject.

* * * * *